United States Patent
Chaudry et al.

(10) Patent No.: US 8,084,461 B2
(45) Date of Patent: Dec. 27, 2011

(54) ALBUTEROL AND IPRATROPIUM INHALATION SOLUTION, SYSTEM, KIT AND METHOD FOR RELIEVING SYMPTOMS OF CHRONIC OBSTRUCTIVE PULMONARY DISEASE

(75) Inventors: Imtiaz Chaudry, American Canyon, CA (US); Partha Banerjee, Plainsboro, NJ (US)

(73) Assignee: Dey, L.P., Napa, CA (US)

( * ) Notice: Subject to any disclaimer, the term of this patent is extended or adjusted under 35 U.S.C. 154(b) by 1239 days.

(21) Appl. No.: 11/037,574

(22) Filed: Jan. 18, 2005

(65) Prior Publication Data

US 2005/0207985 A1 Sep. 22, 2005

Related U.S. Application Data

(63) Continuation-in-part of application No. PCT/US2004/011705, filed on Apr. 15, 2004, and a continuation-in-part of application No. 10/417,723, filed on Apr. 15, 2003, now abandoned, and a continuation-in-part of application No. 10/162,460, filed on Jun. 3, 2002, now Pat. No. 6,632,842, which is a continuation-in-part of application No. 10/034,657, filed on Dec. 28, 2001, now abandoned.

(60) Provisional application No. 60/346,078, filed on Oct. 26, 2001.

(51) Int. Cl.
*A61K 31/44* (2006.01)
(52) U.S. Cl. ........................................................ 514/299
(58) Field of Classification Search ........................ None
See application file for complete search history.

(56) References Cited

U.S. PATENT DOCUMENTS 6,247,617 B1 6/2001 Clyde et al.
6,679,249 B2 * 1/2004 Addington et al. ...... 128/200.14

FOREIGN PATENT DOCUMENTS

WO WO 94/13263 6/1994

OTHER PUBLICATIONS

Asmus, M.A.; Sherman, J.; Hendeles, L.; "Bronchoconstrictor additives in bronchodilator solutions", J Allergy Clin Immunol, 104(2), p. S53-S60, 1999.*
Campbell, S.; "For COPD a Combination of Ipratropium Bromide and Albuterol Sulfate is More Effective than Albuterol Base", Arch Intern Med, 159, p. 156-160, 1999.*
Remington: The Science and Practice of Pharmacy, Nineteenth Edition, 1995, vol. 1, p. 806.*
Coates, AL and Ho, SL, "Drug Adminsitration by Jet Nebulization", Pediatirc Pulmonology, 26, p. 412-423, 1998.*
Tandon et al. "Measuring Nebulizer Output: aerosol Production vs Gravimetric Analysis", Chest 111, p. 1361-65, 1997.*
Combivent(R) Data Sheet, Prepared Mar. 25, 1999.*

(Continued)

*Primary Examiner* — Nissa Westerberg
(74) *Attorney, Agent, or Firm* — Alston & Bird LLP

(57) ABSTRACT

The present invention relates to a dual bronchodilator inhalation solution, system, kit and method for relieving bronchospasm in patients suffering from chronic obstructive pulmonary disease (COPD). In one alternative embodiment, the solution of the present invention is a prepackaged, sterile, premixed, premeasured single unit dose of albuterol and ipratropium bromide for patients suffering from COPD. The present solution may be free of antimicrobial preservatives, such as benzalkonium chloride. In another alternative embodiment, the solution of the present invention comprises about 2.50 mg albuterol and about 0.50 mg ipratropium bromide in a 0.5 ml volume.

14 Claims, 5 Drawing Sheets

OTHER PUBLICATIONS

The Combivnent Inhalation Solution Study Group, Chest, 112, p. 1514-15231, 1997.*

The Merck Index, 10th edition, Merck & Co., Inc.: Rahway, JN 1983, pp. 10, entry 58.

The NIST Reference on Constants, Units, and Uncertainty: International System of Units (SI), SI prefixes, accessed on Dec. 10, 2010 at physics.nist.gov/Units/prefixes.html.

Office Action from related U.S. Appl. No. 11/541,523, mailed Dec. 21, 2010.

Gross, N., et al.:"Inhalation by nebulization of albuterol-ipratropium combination (Dey combination) is superior to either agent alone in the treatment of chronic obstructive pulmonary disease" Respiration, Karger, Basel, CH LNKD D01:10.1159/000029295, vol. 65, No. 5, Sep. 1, 1998, pp. 354-362, XP008103328 ISSN: 0025-7931; p. 355, col. 1, line 1; p. 357, col. 2, paragraph 2.

European Search Report for European Application No. 02789216.5, dated Jun. 18 2010.

Faruk, A. et al., *Effect of Drug Concentration and Permeation Enhancer on Iontophoretic Transport of Salbutamol Sulphate* in vitro, Research Paper, International Journal of Pharmaceutical Sciences and Nanotechnology, vol. 1, Issue 4, Jan.-Mar. 2009, pp. 341-348.

Hakes, L. B. et al., *The Stability of Salbutamol Solution*, J. Pharm. Pharmacol., vol. 31 (Suppl.), (1979), p. 25P.

Hindle, M. et al., *Determination of the Relative Bioavailability of Salbutamol to the Lung Following Inhalation*, Br. J. Clin. Pharmac., vol. 34, (1992), pp. 311-315.

Lipworth, B. J., *Pharmacokinetics of Inhaled Drugs*, Br J Clin Pharmacol, vol. 42 (1996), pp. 697-705.

Malkki, L. et al., *Decomposition of Salbutamol in Aqueous Solutions. I. The Effect of pH, Temperature and Drug Concentration*, International Journal of Pharmaceutics, vol. 63, (1990), pp. 17-22.

Rosethorne, E. M. et al., *Efficacy is a Contributing Factor to the Clinical Onset of Broncodilation of Inhaled $\beta_2$-adrenoceptor Agonists*, Naunyn-Schmied Arch Pharmacol, 382, (2010), pp. 255-263.

Silkstone, V. L. et al., *Determination of the Relative Bioavailability of Salbutamol to the Lungs and Systemic Circulation Following Nebulization*, Br J Clin Pharmacol, vol. 54, (2002), pp. 115-119.

Walker, S. R. et al., *The Clinical Pharmacology of Oral and Inhaled Salbutamol*, Clinical Pharmacology and Therapeutics, vol. 13, No. 6, (1972), pp. 861-867.

DuoNeb™ Inhalation Solution (proposed package insert), NDA 20-950, Center for Drug Evaluation and Research, Dey L.P., Mar. 16, 2001, 25 pages.

*R-Albuterol, Preclinical and Clinical Pharmacology of R-Albuterol, From Molecule to Man*, Clinical Reviews in Allergy and Immunology, vol. 14, (1996) pp. 1-2.

Improved stability in oral delivery of albuterol p . . . [Ann Allergy. 1991]—66(4), p. 324-7, PubMed result [online] [retrieved Oct. 10, 2010]. Retrieved from the Internet: <URL: http://www.ncbi.nlm.nih.gov/pubmed/2014933>. 1 page, Abstract only.

* cited by examiner

FIGURE 7

| | |
|---|---|
| (Albuterol sulfate)<br>Inhalation Solution<br>1.25 mg*3 mL and 0.63 mg*3 mL<br>(*Potency expressed as albuterol, equivalent to 1.5 mg and 0.75 mg albuterol sulfate)<br><br>PATIENT'S INSTRUCTIONS FOR USE<br>Read this patient information completely every time your prescription is filled as information may have changed. Keep these instructions with your medication, as you may want to read them again.<br><br>The inhalation should only be used under the direction of a physician. Your physician and pharmacist have more information about the solution and the condition for which it has been prescribed. Contact them if you have additional questions.<br><br>Storing your medicine<br>Store the inhalation solution between 2 and 25 C (36 and 77 F). Vials should be protected from light before use, therefore, keep unused vials in a foil pouch.<br><br>Dose<br>The inhalation solution is supplied as single-dose, ready-to-use vial containing 3 mL of solution. No mixing or dilution is needed. Use one new vial with each nebulizer treatment.<br>Instructions for Use<br>1. Remove one vial form the foil pouch. Place remaining vials back into foil pouch for storage.<br>2. Twist the cap completely off the vial and squeeze the content into the nebulizer reservoir (Figure).<br><br><br><br>Connect the nebulizer to the mouthpiece or face mask ure 2).<br><br><br><br>4. Connect the nebulizer to the compressor.<br><br>5. Sit in a comfortable, upright position; place the mouthpiece in your mouth (figure 3) or put on the face mask (Figure 4); and turn on the compressor.<br><br><br><br>6. Breathe as calmly, deeply and evenly as possible through your mouth until no more mist is formed in the nebulizer chamber (about 5-15 minutes). At his point, the treatment is finished.<br><br>7. Clean the nebulizer | DOSAGE AND ADMINISTRATION<br>The usual starting dosage for patients 2 to 12 years of age is 1.25 mg or 0.63 mg of albuterol administered 3 or 4 tics daily, as needed, by nebulization. More frequent administration is not recommended. To administer 1.25 mg or 0.63 mg albuterol, use the entire contents of the one unit-dose vial (3 mL of 1.25 mg or 0.63 mg inhalation solution by nebulization). Adjust nebulizer flow rate to deliver solution over 5 to 15 minutes.<br><br>The use of the inhalation solution can be continued as medically indicated to control recurring bouts of bronchospasm. During this time most patients gain optimum benefit for regular use of the inhalation solution.<br><br>Patients 6 to 12 year of age with more sever asthma (baseline FEV1 less than 60% predicted), weight >40kg, or patients 11 to 12 years of age may achieve a better initial response with the 1.25 mg dose.<br><br>HOW SUPPLIED<br><br>The albuterol sulfate inhalation solution is supplied as a 3mL., clear, colorless, sterile, preservative-free, aqueous solution in two different strengths. 0.63 mg and 1.25, of albuterol (equivalent to 0.75 mg of albuterol sulfate or 1.5 mg of albuterol sulfate per 3 mL) in uint-dose low-density polyethylene (LDPE)vials. Each unit-dose LDPE vial is protected in a foil-pouch, and each foil pouch contains 5 unite-dose LDPE vials. Each strength of AccuNeb (albuterol sulfate) inhalation solution is available in a shelf carton containing multiple foil pouches.<br><br>(albuterol sulfate) Inhalation Solution, 0.63 mg (potency expressed as albuterol) contains 0.75 mg albuterol sulfate per 3 mL in unit-dose vial and is available in the following packaging configuration.<br><br>    5 foil pouches, each containing 5 vials, total 25 vials per carton<br><br>(albuterol sulfate) Inhalation Solution, 1.25 mg (potency expressed as albuterol) contains 1.50 mg albuterol sulfate per 3 mL in unit-dose vial and is available in the following packaging configuration.<br><br>    5 foil pouches, each containing 5 vials, total 25 vials per carton<br><br>STORAGE<br><br>Store between 2°C and 25°C (36°F and 77°F) Protect from light and excessive heat.<br><br>Store unit-dose vials in protective foil pouch. |

ALBUTEROL AND IPRATROPIUM INHALATION SOLUTION, SYSTEM, KIT AND METHOD FOR RELIEVING SYMPTOMS OF CHRONIC OBSTRUCTIVE PULMONARY DISEASE

I. CROSS REFERENCE TO RELATED APPLICATIONS

This application is a continuation-in-part of U.S. application Ser. No. 10/417,723, now abandoned, filed Apr. 15, 2003, and is also a continuation-in-part of International Application PCT/US04/011705 filed Apr. 15, 2004. Both applications are continuations-in-part of U.S. application Ser. No. 10/162,460, now U.S. Pat. No. 6,632,842, filed Jun. 3, 2002, which is a continuation-in-part of U.S. application Ser. No. 10/034,657, now abandoned, filed Dec. 28, 2001 (now abandoned), and International Application PCT/US02/33353 filed Oct. 18, 2002, which both claim priority under 35 U.S.C. §119 from U.S. Provisional Application Ser. No. 60/346,078 filed Oct. 26, 2001. The entire disclosure of each of these prior applications is incorporated herein by reference in its entirety. Both above-identified international applications were published in English under PCT Article 2(2) under Publication Nos. WO04/091536 and WO03/037159, respectively.

II. FIELD OF THE INVENTION

The present invention relates to a combination bronchodilator therapy for relieving symptoms associated with chronic obstructive pulmonary disease, and methods of using the same. The present invention also relates to a method of making said combination bronchodilator.

III. BACKGROUND OF INVENTION

Chronic obstructive pulmonary disease (COPD) is a slowly progressive airway disease that produces a decline in lung function that is not fully reversible. The airway limitation in COPD is associated with an abnormal inflammatory response of the lungs to noxious particles or gases.

In the U.S., an estimated 16 million Americans have been diagnosed with some form of COPD, and as many as 16 million others have the condition but have not yet been diagnosed. According to the U.S. Centers for Disease Control and Prevention, COPD is the fourth leading cause of death in the U.S. (behind heart disease, cancer and stroke), claiming the lives of 112,000 Americans annually.

In terms of health care utilization, the number of physician visits for COPD in the U.S. increased from 9.3 million to 16 million between 1985 and 1995. The number of hospitalizations for COPD in 1995 was estimated to be about 500,000. Although prevalence, hospitalization and death rates for COPD are higher in men than women, death rates have risen faster in women in recent years. COPD is clearly a major and growing health care threat in the U.S. and throughout the rest of the world.

In the prior art, antimicrobial agents such as benzalkonium chloride (BAC) are often present in inhalation solutions used to treat COPD. The presence of BAC in these solutions generally does not affect the short-term (single dose) bronchodilator response. However, case reports suggest that repeated use of COPD treatments with BAC may result in paradoxic bronchoconstriction. When inhaled by COPD subjects, BAC may also cause dose-dependent bronchoconstriction. Despite these side effects, many commercially available inhalation solutions contain BAC.

In addition, treatments for COPD often come in multiple dosage units and must be diluted to specific concentrations suitable for treating patients. This poses several problems. For instance, COPD treatments requiring administration of a single dose unit from multiple dosage units sometimes lack proper mixing or diluting instructions, or the instructions for preparing and using the COPD treatment may be hard to follow or can be easily lost. Of even greater import is haphazard diluting or mixing of COPD medications, which can result in administering the wrong dosage. This could be especially harmful for patients less tolerant to higher dosages of asthma medications. Incorrect mixing can also result in treatment failure such that additional medical attention is required, thereby increasing the time, expense and personnel costs associated with therapy.

There is, therefore, a need for an improved inhalation solution, system, kit and method for relieving symptoms associated with COPD.

IV. SUMMARY OF THE INVENTION

One object of the present invention is to provide a dual bronchodilator inhalation solution to relieve bronchospasm in patients suffering from COPD.

Another object of the present invention is to provide a prepackaged, sterile, premixed, premeasured albuterol and ipratropium inhalation solution for the relief of bronchospasm in patients suffering from COPD.

It is yet another object of the present invention to provide a BAC-free albuterol and ipratropium inhalation solution to treat bronchospasm associated with COPD.

A further object of the present invention is to provide a method of administering an albuterol and ipratropium inhalation formulation for relief of bronchospasm associated with COPD.

An additional object of the present invention is to provide a kit and/or system for administering a dual bronchodilator to relieve bronchospasm associated with COPD.

A further object of the present invention is to provide a process for making an albuterol and ipratropium inhalation solution for use in relieving bronchospasm associated with COPD.

Another object of the invention includes a device for use in relieving the symptoms of COPD.

Other objects, features and advantages of the present invention will be apparent to those of ordinary skill in the art in view of the following detailed description of the invention and accompanying drawings.

V. BRIEF DESCRIPTION OF THE DRAWINGS

FIG. 7 depicts a non-limiting example of a label utilized in the present invention.

VI. DETAILED DESCRIPTION OF THE INVENTION

Albuterol

Figure 1:
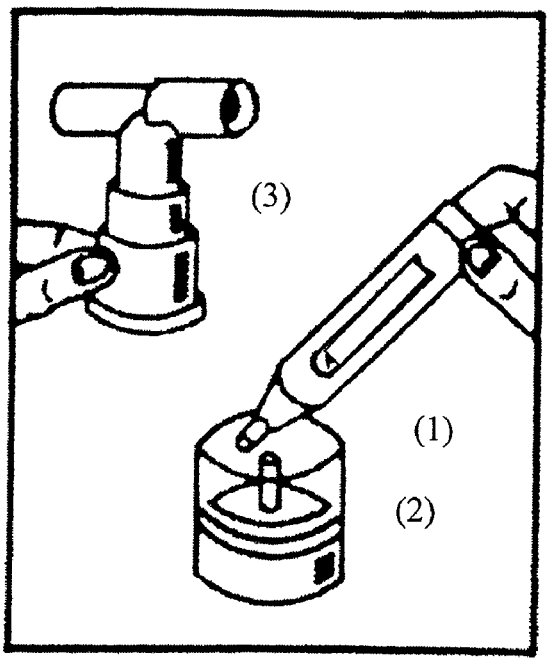
FIGS. 1-4 depict a non-limiting example of administering the inhalation solution of the present invention by a nebulizer.
Figure 2:
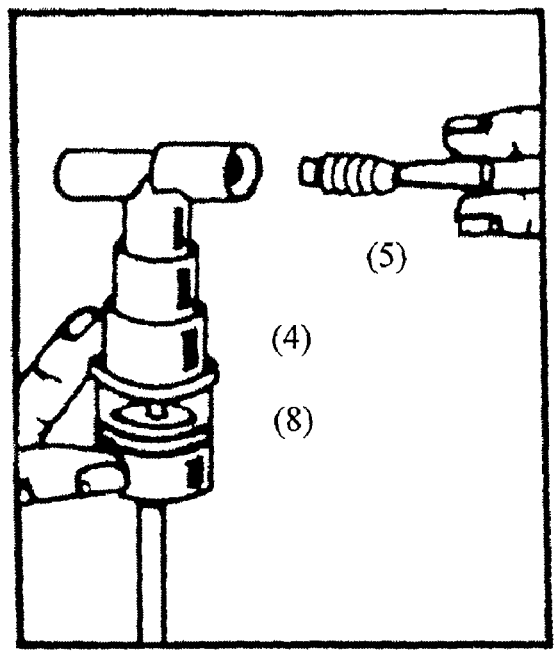
Figure 3:
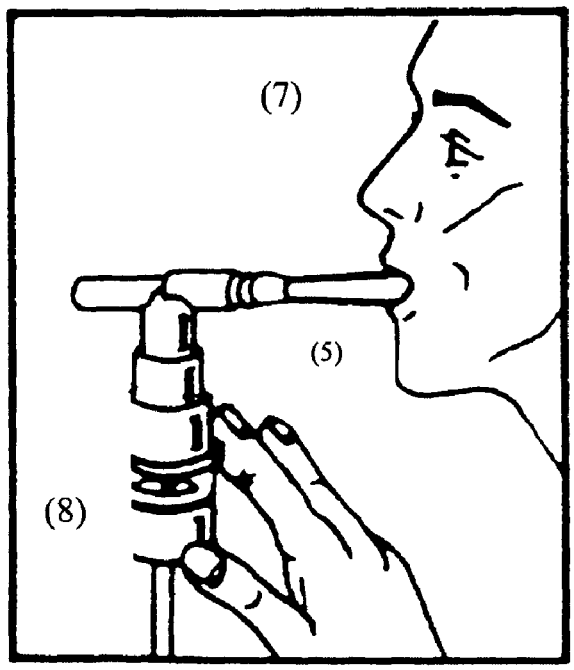
Figure 4:
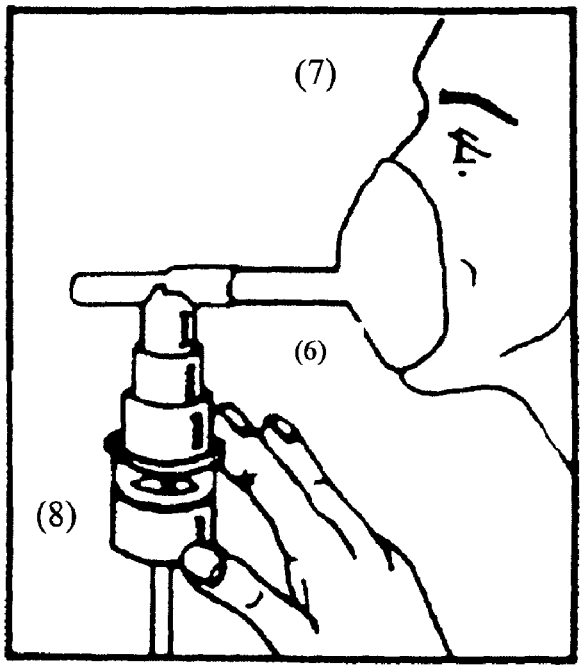

The present invention relies on the bronchodilation effects of albuterol to provide relief from symptoms associated with COPD. As used herein, the term "albuterol" includes, but is not limited to, any form of albuterol that is capable of producing a desired bronchodilation effect in patients, including, but not limited to, all tautomeric forms, enantomeric forms, stereoisomers, anhydrides, acid addition salts, base salts, solvates, analogues and derivatives of albuterol, or any mixture thereof.

In the present invention, acceptable salts of albuterol may include, but are not limited to, hydrochloride, sulfate, maleate, tartrate, citrate and the like. These salts are described in U.S. Pat. No. 3,644,353, which is incorporated herein by reference in its entirety.

In the present invention, the preferred salt of albuterol is sulfate. In an alternative embodiment, the inhalation solution of the present invention comprises the sulfate salt of racemic albuterol, or it may comprise at least substantially of a single isomer of albuterol. Albuterol sulfate is a relatively selective beta-2-adrenergic bronchodilator with an empirical formula of $C_{13}H_{21}NO_3$. The chemical name for albuterol sulfate is $\alpha^1$-[(tert-butylamino)methyl]-4-hydroxy-m-xylene-$\alpha,\alpha'$-diol sulfate (2:1)(salt), and its established chemical structure is as follows:

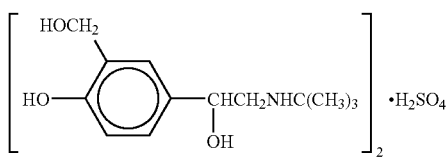

Ipratropium

The present invention also relies on the bronchodilation effect of ipratropium to provide relief from symptoms associated with COPD. Ipratropium is an anticholinergic bronchodilator. As used herein, the term "ipratropium" includes, but is not limited to, any form of ipratropium which is capable of producing a desired bronchodilation effect in patients suffering from COPD, including, but not limited to, all tautomeric forms, enantomeric forms, stereoisomers, anhadrides, acid addition salts, base salts, salvates, analogues, derivatives of ipratropium, or any mixture thereof.

In the present invention, acceptable salts of ipratropium may include, but are not limited to, halide salts such as bromide, chloride and iodide. These and other acceptable salts are described in U.S. Pat. No. 3,505,337, which is incorporated herein by reference in its entirety. In one alternative embodiment, the inhalation solution of the present invention comprises racemic ipratropium bromide, or it may comprise at least substantially of a single isomer of ipratropium bromide.

In one embodiment of the present invention, the preferred salt of ipratropium is bromide, which is chemically described as 8-azoniabicyclo [3.2.1]-octane, 3-(3, hydroxyl-1-oxo-2-phenylpropoxy)-8methyl-8-(1-methylethyl)-bromide, monohydrate, (endo, syn)-, (±)-. Ipratropium bromide has a molecular weight of 430.4 and the empirical formula $C_{20}H_{30}BrNO_3.H_2O$. It is freely soluble in water and lower alcohol, and is insoluble in lipohilic solvents such as ether, chloroform and fluorocarbon. The established chemical structure of ipratropium bromide is as follows:

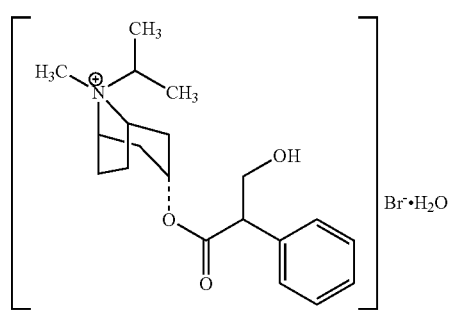

In the present invention, the albuterol and ipratropium may be provided in a variety of pharmaceutically acceptable vehicles, including, but not limited to, water or any other aqueous solution comprising a pharmaceutically acceptable amount of an osmotic agent.

In one alternative embodiment, the inhalation solution of the present invention comprises a therapeutically effective amount of albuterol and ipratropium. As used herein, the phrase "therapeutically effective amount of albuterol and/or ipratropium" means a safe and tolerable amount of both compounds, as based on industry and/or regulatory standards. Such amount being sufficient to effectively induce bronchodilation and/or provide relief of bronchospasm in patients suffering form COPD.

In the inhalation solution of the present invention, a therapeutically effective amount of albuterol may include from about 0.63 mg to about 4.2 mg albuterol. Here, the potency of the albuterol is equivalent to from about 0.75 mg to about 5 mg of albuterol sulfate. In an alternative embodiment, a therapeutically effective amount of albuterol may include about 2.5 mg albuterol.

In another alternative embodiment of the present invention, a therapeutically effective amount of albuterol may include from about 0.60 mg to about 5.0 mg albuterol, including the following intermediate ranges of albuterol: about 0.60 mg to about 0.70 mg; about 0.71 mg to about 0.80 mg; about 0.81 mg to about 0.90 mg; about 0.91 mg to about 1.00 mg; about 1.01 mg to about 1.10 mg; about 1.11 mg to about 1.20 mg; about 1.21 mg to about 1.30 mg; about 1.31 mg to about 1.40 mg; about 1.41 mg to about 1.50 mg; about 1.51 mg to about 1.60 mg; about 1.61 mg to about 1.70 mg; about 1.71 mg to about 1.80 mg; about 1.81 mg to about 1.90 mg; about 1.91 mg to about 2.00 mg; about 2.01 mg to about 2.10 mg; about 2.11 mg to about 2.20 mg; about 2.21 mg to about 2.30 mg; about 2.31 mg to about 2.40 mg; about 2.41 mg to about 2.50 mg; about 2.51 mg to about 2.60 mg; about 2.61 mg to about 2.70 mg; about 2.71 mg to about 2.80 mg; about 2.81 mg to about 2.90 mg; about 2.91 mg to about 3.00; about 3.01 to about 3.10; about 3.11 to about 3.20; about 3.21 to about 3.30 mg; about 3.31 mg to about 3.40 mg; about 3.41 mg to about 3.50 mg; about 3.51 mg to about 3.60 mg; about 3.61 to about 3.70 mg; about 3.71 to about 3.80 mg; about 3.81 mg to about 3.90 mg; about 3.91 mg to about 4.0 mg; about 4.01 mg to about 4.10 mg; about 4.11 mg to about 4.20 mg; about 4.21 mg to about 4.30 mg; about 4.31 mg to about 4.40 mg; about 4.41 mg to about 4.50 mg; about 4.51 mg to about 4.60 mg;

about 4.61 mg to about 4.70 mg; about 4.71 mg to about 4.80 mg; about 4.81 mg to about 4.90 mg; about 4.91 mg to about 5.00 mg.

In another alternative embodiment of the present invention, a therapeutically effective amount of albuterol may include from about 0.75 mg to about 5.0 mg albuterol sulfate, including the following intermediate amounts: about 0.75 mg to about 0.80 mg; about 0.81 to about 0.90 mg; about 0.91 mg to about 1.00 mg; about 1.01 mg to about 1.10 mg; about 1.11 mg to about 1.20 mg; about 1.21 mg to about 1.30 mg; about 1.31 mg to about 1.40 mg; about 1.41 mg to about 1.50 mg; about 1.51 mg to about 1.60 mg; about 1.61 mg to about 1.70 mg; about 1.71 mg to about 1.80 mg; about 1.81 mg to about 1.90 mg; about 1.91 mg to about 2.00 mg; about 2.01 mg to about 2.10 mg; about 2.11 mg to about 2.20 mg; about 2.21 mg to about 2.30 mg; about 2.31 mg to about 2.40 mg; about 2.41 mg to about 2.50 mg; about 2.51 mg to about 2.60 mg; about 2.61 mg to about 2.70 mg; about 2.71 mg to about 2.80 mg; about 2.81 mg to about 2.90 mg; about 2.91 mg to about 3.00; about 3.01 to about 3.10; about 3.11 to about 3.20; about 3.21 to about 3.30 mg; about 3.31 mg to about 3.40 mg; about 3.41 mg to about 3.50 mg; about 3.51 mg to about 3.60 mg; about 3.61 to about 3.70 mg; about 3.71 to about 3.80 mg; about 3.81 mg to about 3.90 mg; about 3.91 mg to about 4.0 mg; about 4.01 mg to about 4.10 mg; about 4.11 mg to about 4.20 mg; about 4.21 mg to about 4.30 mg; about 4.31 mg to about 4.40 mg; about 4.41 mg to about 4.50 mg; about 4.51 mg to about 4.60 mg; about 4.61 mg to about 4.70 mg; about 4.71 mg to about 4.80 mg; about 4.81 mg to about 4.90 mg; about 4.91 mg to about 5.00 mg.

In another alternative embodiment of the present invention, a therapeutically effective amount of albuterol may include from about 0.020% to about 0.14% by weight albuterol, including the following intermediate ranges: about 0.020 wt % to about 0.029 wt %; about 0.030 wt % to about 0.039 wt %; about 0.040 wt % to about 0.049 wt %; about 0.050 wt % to about 0.059 wt %; about 0.060 wt % to about 0.069 wt %; about 0.070 wt % to about 0.079 wt %; about 0.080 wt % to about 0.089 wt %; about 0.090 wt % to about 0.099 wt %; about 0.10 wt % to about 0.14 wt %.

In another alternative embodiment, a therapeutically effective amount of albuterol may include from about 0.1% to about 5.0% by weight albuterol, including the following intermediate ranges: about 0.2% to about 0.5%; about 0.5% to about 0.75%; about 0.75% to about 1.0%; 1.0% to about 1.25%; about 1.25% to about 1.50%; 1.50% to about 1.75%; 1.75% to about 2.0%; about 2.0% to about 2.25%; about 2.25% to about 2.50%; 2.50% to about 2.75%; to about 2.75% to about 3.0%; about 3.0% to about 3.5%; about 3.5% to about 4.0%; 4.0% to about 4.5%; about 4.5% to about 5.0%. In alternative embodiment, the present invention comprises 1.25% albuterol base (equivalent to 1.5% albuterol sulfate.

In yet another alternative embodiment of the present invention a therapeutically effective amount of albuterol may include from about 0.025% to about 0.17% by weight albuterol sulfate, including the following intermediate ranges: about 0.025 wt % to about 0.029 wt %; about 0.030 wt % to about 0.039 wt %; about 0.040 wt % to about 0.049 wt %; about 0.050 wt % to about 0.059 wt %; about 0.060 wt % to about 0.069 wt %; about 0.070 wt % to about 0.079 wt %; about 0.080 wt % to about 0.089 wt %; about 0.090 wt % to about 0.099 wt %; about 0.10 wt % to about 0.17 wt %.

In another alternative embodiment of the present invention, a therapeutically effective amount of ipratropium bromide may include from about 0.01 mg to about 1.0 mg of ipratropium bromide. Such therapeutically effective amount may also include the following intermediate ranges of ipratropium bromide: about 0.01 mg to about 0.02 mg; about 0.02 mg to about 0.04 mg; about 0.05 to about 0.07 mg; about 0.08 mg to about 0.10 mg; about 0.11 mg to about 0.13 mg; about 0.14 mg to about 0.16 mg; about 0.17 mg to about 0.19 mg; about 0.20 mg to about 0.22 mg; 0.23 mg to about 0.25 mg; 0.26 mg to about 0.28 mg; about 0.29 mg to about 0.31 mg; about 0.32 to about 0.34 mg; about 0.35 mg to about 0.37 mg; about 0.36 mg about 0.38 mg; about 0.39 mg to about 0.41 mg; about 0.42 mg to about 0.44 mg; about 0.45 mg to about 0.47 mg; about 0.48 mg to about 0.50 mg; about 0.51 mg to about 0.53 mg; about 0.54 mg to about 0.56 mg; about 0.57 mg to about 0.59 mg; about 0.60 mg to about 0.62 mg; about 0.63 mg to about 0.65 mg; about 0.66 mg to about 0.68 mg; about 0.69 mg to about 0.71 mg; about 0.72 mg to about 0.74 mg; about 0.75 mg to about 0.77 mg; about 0.79 mg to about 0.81 mg; about 0.82 mg to about 0.84 mg; about 0.85 mg to about 0.87 mg; about 0.88 mg to about 0.91 mg; about 0.92 mg to about 0.94 mg; about 0.95 mg to about 0.97 mg; about 0.98 mg to about 1.00 mg.

In another alternative embodiment of the present invention, a therapeutically effective amount of ipratropium may include from about 0.001% to about 0.030% by weight ipratropium bromide, including the following intermediate ranges of ipratropium bromide: about 0.001 wt % to about 0.005 wt %; about 0.006 wt % to about 0.010 wt %; about 0.011 wt % to about 0.015 wt %; about 0.016 wt % to about 0.020 wt %; about 0.021 wt % to about 0.025 wt %; 0.026 wt % to about 0.030 wt %.

Most pharmaceutical inhalation solutions contain the antimicrobial agent BAC. One problem with these solutions is that the BAC may cause paradoxic bronchoconstriction if the solution is administered repeatedly over short intervals. Another problem is that, when inhaled by patients, the BAC can cause dose-dependent bronchoconstriction. The inhalation solution of the present invention may be provided without BAC, thereby making it suitable, especially in an emergency situation, where the inhalation solution is administered repeatedly over a short period of time. Also, administering a BAC-free inhalation solution to a patient reduces the concomitant liability of adverse effects associated with BAC. It also reduces the toxicity and other side effects associated with BAC.

The inhalation solution of the present invention may also be provided in sterile, unit dose treatments, thus eliminating the need to include BAC in the solution. Moreover, as shown in Table 1, in its sterile form the formulation of the present invention (which comprises a therapeutically effective amount of albuterol sulfate and ipratropium bromide) provides a stable inhalation solution such that the formulation can be stored (e.g., on a shelf) for long periods of time.

TABLE 1

Stability Data

| | | 0.083 wt % Albuterol Sulfate and 0.017 wt % Ipratropium Bromide | | | |
|---|---|---|---|---|---|
| | | Assay* | | | |
| | | Albuterol sulfate | Ipratropium bromide | pH | Osmolality (mOsm/kg) |
| Time zero | | 98 | 98 | 3.3 | 283 |
| 25° C./35% RH | 12 months | 105 | 99 | 3.4 | 285 |
| | 24 months | 102 | 101 | 3.5 | 282 |
| 40° C./15% RH | 3 months | 100 | 99 | 3.5 | 284 |
| | 6 months | 103 | 102 | 3.4 | 283 |

*as percent of label claim (0.083 wt % albuterol sulfate and 0.017 wt % ipratropium bromide)

As stated, the compositions provided herein are stable. For example, the compositions provided herein are stored between about 15° C. and about 30° C., and remain stable for a relatively long period of time. In one embodiment, the compositions are stored at 25° C.

In another embodiment, the stability of the compositions provided herein may contain greater than 80%, 85%, 90% or 95% of the initial amount of active ingredient, e.g., Albuterol and Ipratropium at a given temperature for a long period of time. Thus, for example, a composition that is stable for 30 days at 25° C. would have greater than 80%, 85%, 90% or 95% of the initial amount of active ingredients present in the composition at 30 days following storage at 25° C.

In another embodiment, the compositions herein are stable during long term storage, in that the compositions are suitable for administration to a subject in need thereof when they have been stored for a length of time (i.e., shelf-life) for a period greater than 1, 2 or 3 years at 25° C. In other embodiments herein, using Arrhenius Kinetics, >80% or >85% or >90% or >95% estimated bronchodilating agent remains after such storage, for example.

Other indications of the stability of the present compositions can be shown in terms of by-products or degradation products present over time, as shown in Tables 2 and 3 below.

TABLE 2

| | Albuterol degradation products/related compounds as % of albuterol | Range at 6 to 24 months at 25° C. | Range in drug substance |
|---|---|---|---|
| 1 | 5-2-((1,1-Dimethyl-ethyl)amino-1-hydroxyethyl)-2-hydroxybenzaldehyde | ND-0.012% w/w | |
| 2 | Bis-(2-hydroxy0-5-(2-tertbutylamino-1-hydroxyethyl)phenyl-methyl ether | | 0.09-0.174% w/w |
| 3 | 2-tert-butylamino-1-(4-hydroxy-3-methoxy-methylphenyl)-ethanol | | 0.01-0.12% w/w |
| 4 | Tert-butylamino-3-chloro-4-hydroxy-5-hydroxymethyl-acetophenone | | ND-0.0002% w/w |
| 5 | Tert-butylamino-4-hydroxy-5-hydroxy-methylacetophenone | | ND-0.002% w/w |
| 6 | 1-(4-hydroxy-3-methylphenyl)-2-(tert-butylamino) ethanol | | 0.0009-0.036% w/w |

TABLE 2-continued

| | Albuterol degradation products/related compounds as % of albuterol | Range at 6 to 24 months at 25° C. | Range in drug substance |
|---|---|---|---|
| 7 | 1-(5-chloro-4-hydroxy-3-hydroxy-methylphenyl)-2-(tert-butylamino) ethanol | | ND |
| 8 | Unknown 1 | ND-0.07% by peak area | |
| 9 | Any other unknown | ND-0.025% by peak area | |
| 10 | Total | 0.18-0.23% | |

ND = none detected

TABLE 3

| | Ipratropium degradation products/related compounds as % of ipratropium bromide | Range at up to 24 months at 25° C. | Range in drug substance |
|---|---|---|---|
| 1 | Tropic acid | ND-0.08% w/w | |
| 2 | 8S-ipratropium bromide | | ND-0.058% w/w |
| 3 | N-isopropyl-noratropine | | ND |
| 4 | Ipratropium alcohol | ND-0.038% w/w | |
| 5 | Any other unknown | ND | |
| 6 | Atropic acid | ND | |
| 7 | Total (excluding APO-ipratropium) | ND-0.2% | |

ND = none detected

In one embodiment, the compositions herein are at least substantially clear, based on color measurement tests set forth by the America Public Health Association ("APHA"). In another embodiment of the present invention, the APHA color results for compositions herein at up to 24 months at 25° C. ranged from 0 to 5 units (mostly 0 units), as based on APHA standards.

In one embodiment, the process of the present invention provides compositions having an albuterol content of about 2.5 mg to about 2.75 mg per vial. In another alternative embodiment, the process of the present invention provides compositions having an Ipratropium content of about 0.45-0.55 mg per vial. In yet another alternative embodiment, the process of the present invention provides an average fill volume of about 2.84 to about 3.30 ml into each vial.

In another alternative embodiment, the compositions of the present invention may contain minimal amounts of contaminants including, but not limited to the following (where the term "NMT" means "not more than"):

TABLE 4

| 1. Volatiles | |
| --- | --- |
| Acetone | about NMT 0.2 mcg/mL or less |
| ethyl acetate | about NMT 0.3 mcg/mL or less |
| n-heptane | NMT 0.1 mcg/mL or less |
| n-propylacetate | NMT 0.3 mcg/mL or less |
| Toluene | NMT 0.3 mcg/mL or less |
| 2-butanone | none detected (signal/nose NMT 3) |
| Unknowns | |
| 2. Leachables | |
| Irganox 129 | none detect (NMT 0.02 mcg/mL) |
| Extractable 1 | none detected (signal/noise NMT 3) |
| Extractable 2 | none detected (signal/noise NMT 3) |
| Unknowns | none detected (signal/noise NMT 3) |

In another alternative embodiment, compositions of the present invention may contain minimal amounts of particulate matter, including, but not limited to the following: NMT about 1000 to 5000, preferably about 3800 particles/vial >2 Φm; NMT about 10 to 100, preferably about 80 particles/vial >10 Φm; or NMT about 1 to 5, preferably about 3 particles/vial >25 Φm.

In another embodiment of the present invention, the inhalation solution may have a pH of about 2.0 to about 8.0. In another embodiment of the claimed invention, the solution may have a pH of about 3.0 to about 4.0, preferably a pH of about 3.5. The pH may be adjusted with 1N hydrochloric acid or 1N sulfuric acid. The inhalation solution of the present invention may also contain sodium citrate at a concentration of about 0.1 to 0.5% (w/w), preferably about 0.2% (w/w/) to control pH or may further contain a buffer. General and biological buffers in the pH range of about 2.0-8.0 include but are not limited to the following: acetate, barbital, borate, Britton-Robinson, cacodylate, citrate, collidine, formate, maleate, McIlvaine, phosphate, Prideaux-Ward, succinate, citrate-phosphate-borate (Teorell-Stanhagen), veronal acetate, MES, BIS-TRIS, ADA, ACES, PIPES, MOPSO, BIS-TRIS PROPANE, BES, MOPS, TES, HEPES, DIPSO, MOBS, TAPSO, TRIZMA, HEPPSO, POPSO, TEA, EPPS, TRICINE, GLY-GLY, BICINE, HEPBS, TAPS, and AMPD buffers.

In another embodiment of the present invention, the osmolality of the inhalation solution may be adjusted from about 150 to about 550 mOsm/kg. In other embodiments of the present invention, the osmolality of the solution may be from about 275 to about 325 mOsm/kg. In yet another embodiment, the composition may have an osmolality of about 290 mOsm/kg. Tonicity adjusting agents include but are not limited to the following excipients: ammonium carbonate, ammonium chloride, ammonium lactate, ammonium nitrate, ammonium phosphate, amonium sulfate, ascorbic acid, bismuth sodium tartrate, boric acid, calcium chloride, calcium disodium edetate, calcium gluconate, calcium lactate, citric acid, dextrose, diethanolamine, dimethyl sulfoxide, edetate disodium, edetate trisodium monohydrate, fluorescein sodium, fructose, galactose, glycerin, lactic acid, lactose, magnesium chloride, magnesium sulfate, manitol, polyethyne glycol, potassium acetate, potassium chlorate, potassium chloride, potassium iodide, potassium nitrate, potassium phosphate, potassium sulfate, propylene glycol, silver nitrate, sodium acetate, sodium bicarbonate, sodium biphosphate, sodium bisulfite, sodium borate, sodium bromide, sodium cacodylate, sodium carbonate, sodium chloride, sodium citrate, sodium iodide, sodium lactate, sodium metabisulfite, sodium nitrate, sodium nitrite, sodium phosphate, sodium propionate, sodium succinate, sodium sulfate, sodium sulfite, sodium tartrate, sodium thiosulfate, sorbitol, sucrose, tartaric acid, triethanolamine, urea, urethan, uridine, and zinc sulfate.

In one embodiment, the inhalation solution of the present invention is sterile. A benefit of a sterile inhalation solution is that it reduces the possibility of introducing contaminants into the patient when administered, thereby reducing the chance of an opportunistic infection in the patient.

Non-adherence to COPD medication therapy and medication error are considerable problems. These problems can be significantly reduced by providing COPD patients a prepackaged, premixed, premeasured amount of albuterol and ipratropium. Providing these compounds in this fashion makes COPD therapy simple because it increases convenience and eliminates confusion in preparing appropriate dosages. These advantages are especially significant where treatments often come in multiple dosage units and must be diluted to specific concentrations suitable for treating patients. As discussed previously, this poses several problems.

The present invention overcomes the aforementioned problems by providing therapeutically effective amounts of both albuterol and ipratropium in prepackaged, premixed, premeasured and/or unit dose amounts. In one embodiment, the present invention comprises one or more prefilled containers. The one or more containers each comprising a single unit dose of an aqueous solution comprising a therapeutically effective amount of albuterol and ipratropium for the treatment of COPD. Providing the inhalation solution in such a manner eliminates the need to dilute or mix COPD medications to obtain proper dosages for treatment. Also, no special pharmacy compounding is required, thereby reducing the chance of medication errors. Further, there is a lower risk of cross-contamination, and less waste of medication when providing an inhalation solution in a premixed, ready to use form.

Other features of the present invention include improved user compliance and quality of life as compared to conventional treatments for COPD. While the level of compliance of any COPD treatment depends in part on the motivation of the user and the skill of the individual dispensing the treatment, compliance nevertheless may be improved by controlling factors such as the ease with which the treatment may be administered, as well as the desirability of receiving the treatment.

The present invention provides a convenient, fast and reliable treatment for COPD and clearly represents an improvement over traditional COPD treatments. Also, the present invention is designed to facilitate user compliance by providing one or more dispensing containers comprising a premixed, premeasured inhalation solution comprising a single unit dose of a therapeutically effective amount of albuterol and ipratropium for the treatment of COPD. Such containers may be utilized in a method of treating COPD or the containers may be incorporated in a system and/or kit for treating the same.

In one alternative embodiment, the present invention is a sterile, premixed, premeasured, BAC-free inhalation solution comprising a single unit dose of a therapeutically effective amount of albuterol and ipratropium in a single container. Each unit dose container comprises 3.0 mg/3 ml of albuterol sulfate (equivalent to 2.5 mg of albuterol) and 0.5 mg ipratropium bromide in a sterile, aqueous solution. Sodium chloride may be added to make the solution isotonic and hydrochloric acid may be added to adjust pH of the solution to about 4.0. The inhalation solution of the present invention may or may not include a chelating agent, such as EDTA.

In another alternative embodiment, the inhalation solution of the present invention may be supplied as a 3 ml, sterile, BAC-free, nebulizer solution comprising from about 0.20 to about 0.5 mg ipratropium bromide and from about 0.75 mg/3 ml to about 3.0 mg/3 ml of albuterol sulfate. The nebulizer solution is contained in a unit-dose, low-density polyethylene (LDPE) container. Each unit-dose container may be disposed in a foil pouch, and each foil pouch may contain 5 or more unit-dose containers. Each foil pouch containing the unit dose container may be disposed in a shelf carton.

The present invention provides an albuterol and ipratropium inhalation solution for treating different stages of COPD, including but not limited to, stages 0 to III. Some characteristics associated with the different stages of COPD are shown in Table 2. The information in this table is presented for illustrative purposes only. It is not intended to limit the scope of the invention.

TABLE 2

| Stage | Severity | Description |
|---|---|---|
| 0 | At risk | Normal spirometry |
|   |   | Chronic symptoms (cough, sputum production) |
| I | Mild | $FEV_1/FVC < 70\%$ |
|   |   | $FEV_1 > 80\%$ predicted |
|   |   | With or without chronic symptoms |
| II | Moderate | $FEV_1/FVC < 70\%$ |
|   |   | $30\% \geqq FEV_1 < 80\%$ predicted |
|   |   | (IIA: $50\% \geqq FEV_1 < 80\%$) |
|   |   | (IIB: $30\% \geqq FEV_1 < 50\%$) |
|   |   | With or without chronic symptoms |
| III | Severe | $FEV_1/FVC < 70\%$ |
|   |   | $FEV_1 < 30\%$ predicted or less than 50% |
|   |   | predicted with respiratory failure or |
|   |   | clinical signs of right heart failure. |

In the present invention, a therapeutically effective amount of albuterol and ipratropium is administered to induce bronchodilation and/or provide relief of bronchospasm associated with COPD. Such amount of albuterol and ipratropium may be administered to a patient after the onset of bronchospasm to reduce breathing difficulties resulting from COPD. In another embodiment, the albuterol and ipratropium may be administered prophylactically, that is, to prevent COPD progression.

The quantity of albuterol and ipratropium to be administered will be determined on an individual basis, and will be based at least in part on consideration of the patient's size, the severity of the symptoms to be treated, and the results sought. The actual dosage (quantity of albuterol and ipratropium administered at a time) and the number of administrations per day will depend on the mode of administration, such as inhaler, nebulizer or oral administration. For example, about 2.5 mg of albuterol and about 0.5 mg of ipratropium bromide administered by nebulization 4 times per day with up to 2 additional 3 ml doses allowed per day, if needed, would be adequate to produce the desired bronchodilation effect in most patients.

Further, the albuterol and ipratropium inhalation solution of the present invention may be administered together with one or more other drugs. For example, an antiasthmatic drug such as theophylline or terbutaline, or an antihistamine or analgesic such as aspirin, acetaminophen or ibuprofen, may be administered with or in dose temporal proximity to administration of a therapeutically effective amount of albuterol. The present invention and the one or more drugs may be administered in one formulation or as two separate entities. According to the present invention, a therapeutically effective amount of albuterol and ipratropium, alone or in combination with another drug(s), may be administered to a individual periodically as necessary to reduce symptoms of COPD.

In another alternative embodiment, the inhalation solution of the present invention may be administered by nebulizer. Such nebulizer including, but not limited to, a jet nebulizer, ultrasonic nebulizer and breath actuated nebulizer. Preferably, the nebulizer is a jet nebulizer connected to an air compressor with adequate airflow. The nebulizer being equipped with a mouthpiece or suitable face mask. Specifically, a PARI-LC-PLUS™ nebulizer (with face mask or mouthpiece) connected to a PRONEB™ compressor may be used to deliver the inhalation solution of the present invention to a patient. In an embodiment, the inhalation solution may be administered by nebulizers manufactured, designed or sold by Omron, such as the Omron MICRO AIR® Ultrasonic Nebulizer. Other nebulizers may also include those manufactured, designed, or sold by Aerogen.

In an alternative embodiment, the system and/or kit of the present invention comprises an inhalation solution comprising a therapeutically effective amount of albuterol and ipratropium in a prepackaged, premeasured, premixed and/or single unit dose form for the treatment of COPD. The inhalation solution may be sterile and/or BAC-free.

In another embodiment, the present invention provides a system and/or kit for organizing and storing one or more prefilled dispensing containers, each container comprising a premixed, premeasured inhalation solution. The inhalation solution comprising a single unit dose of a therapeutically effective amount of albuterol and ipratropium. Such system and/or kit may provide such containers in prepackaged form. The one or more containers may be comprised of plastic including, but not limited to, a semi-permeable plastic such as LDPE. The container may also comprise a TWIST-FLEX® top, such top comprising an easy-to-grip tab-like handle such that the container may be opened, for example, by twisting off the tab by hand. The TWIST-FLEX® top is advantageous in that it allows for easy dispensing of the solution, prevents spillage and eliminates the need to open the container or tearing by cutting or tearing off the top, or the like, thereby reducing cross-contamination. In one alternative embodiment, the design of the container substantially conforms to those designs illustrated in U.S. Pat. Des. Nos. 317,715; 296, 869; 289,609; or 275,732, which are incorporated herein by reference. One or more of the semi-permeable single unit dose containers may be prepackaged in aluminum foil pouch, such that the foil provides a protective barrier against environmental contaminants and light. Such a barrier improves the shelf-life and stability of the inhalation solution.

In another alternative embodiment, the present invention comprises a prepackaged inhalation system and/or kit suitable for patients suffering from COPD. Such prepackaged system and/or kit comprising: (a) one or more single unit dosages of a therapeutically effective amount of albuterol and ipratropium; (b) administration instructions for the use of said unit dose as a treatment for COPD; and (c) a dispensing container prefilled with the one or more unit doses of albuterol and ipratropium.

In another alternative embodiment, the prepackaged inhalation system and/or kit of the present invention provides one or more premixed, premeasured single unit dose vials comprising a therapeutically effective amount of albuterol and ipratropium for the treatment of bronchospasm associated with COPD, and instructions for using the same.

In one alternative embodiment, the present invention is directed to a system for reducing medication error and enhancing therapeutic compliance of an individual suffering from chronic obstructive pulmonary disease, the prepackaged therapeutic system comprising:

(a) one or more dispensing containers; the one or more containers each prefilled with about 0.1 ml to about 2.0 ml or 3 ml of a sterile, benzlakonium chloride-free, premixed, premeasured aqueous inhalation solution comprising a unit dose of a therapeutically effective amount of albuterol and ipratropium bromide; wherein the dosage of albuterol is about 2.5 mg and the dosage of ipratropium bromide is about 0.5 mg; the inhalation solution in each of the one or more containers is suitable for nebulization in a nebulizer; the inhalation solution in each of the one or more containers has a long shelf life;

(b) one or more labels with indicia thereon, the indicia comprising efficacy dosage, administration, contraindication and adverse reaction data pertaining to the inhalation solution in each of the one or more containers;

(c) wherein the contraindication data comprises data indicating that the inhalation solution in each of the one or more containers is contraindicated for humans with hypersensitivity to atropine and derivatives thereof; and (d) wherein the adverse reaction data comprises data indicating that precipitation or worsening of narrow-angle glaucoma, acute eye pain, blurred vision, paradoxical bronchospasm, wheezing, exacerbation of chronic obstructive pulmonary disease symptoms, drowsiness, aching, flushing, upper respiratory tract infection, palpitations, taste perversion, elevated heart rate, sinusitis, back pain and sore throat may occur after administrating the inhalation solution in the one or more containers.

The dosage and administration data may comprise data indicating that the recommended dose of the inhalation solution in each of the one or more containers is about 2.5 mg of albuterol and about 0.5 mg impratropium bromide in 3 ml of an aqueous solution administered 4 times per day by nebulization with up to 2 additional recommended doses allowed per day, if needed. Also, the adverse reaction data may comprise data indicating that immediate hypersensitivity reactions to the inhalation solution in each of the one or more containers may occur after administration of the inhalation solution, said hypersensitivity reactions comprising urticaris, angioedema, rash, pruritis, oropharyngeal, edema, bronchospasm, and anaphylaxis. The adverse reaction data may also comprise data indicating that allergic-type reactions may occur after administrating the inhalation solution in the one or more containers, including skin rash, pruritis, and urticaria. The adverse reaction data may further comprise data indicating a list of one or more adverse events that may occur after administrating the inhalation solution, said adverse events including chest pain, diarrhea, dyspepsia, nausea, leg cramps, bronchitis, lung disease, pharyngitis, pneumonia, and urinary tract infection.

In another alternative embodiment, the present prepackaged therapeutic system and/or kit for treating bronchospasm in a patient suffering from chronic obstructive pulmonary disease may comprise.

(a) one or more dispensing containers; the one more containers each prefilled with 3 ml of a sterile, stable, premixed, premeasured aqueous inhalation solution free of benzalkonium chloride; the inhalation solution consisting of sodium chloride, water, edetate disodium, an acid to adjust the pH of the inhalation solution to about 4, and a unit dose of a therapeutically effective amount of albuterol and ipratropium bromide, wherein the amount of albuterol is about 2.50 mg and the amount of ipratropium bromide is about 0.5 mg; the inhalation solution in each of the one or more containers is suitable for nebulization in a nebulizer; said inhalation solution having a long shelf life;

(b) one or more labels with indicia thereon; the indicia comprising efficacy, dosage, administration, contraindication and adverse reaction information pertaining to the inhalation solution in each of the one or more containers;

(c) wherein the dosage and administration data comprises data indicating that the recommended dose of the inhalation solution in each of the one or more containers is about 2.5 mg of albuterol and about 0.5 mg impratropium bromide in 3 ml of an aqueous solution administered 4 times per day by nebulization with up to 2 additional recommended doses allowed per day, if needed;

(d) wherein the contraindication data comprises data indicating that the inhalation solution in each of the one or more containers is contraindicated for humans with hypersensitivity to atropine and derivatives thereof;

(e) wherein the adverse reaction data comprises data indicating that immediate hypersensitivity reactions to the inhalation solution in each of the one or more containers may occur after administrating the inhalation solution, said hypersensitivity reaction including urticaris, angioedema, rash, pruritis, oropharyngeal, edema, bronchospasm, and anaphylaxis;

(f) wherein the adverse reaction data comprises data indicating that allergic-type reactions may occur after administrating the inhalation solution in the one or more containers; said allergic type reaction, including skin rash, pruritis, and urticaria;

(g) wherein the adverse reaction data comprises data indicating that precipitation or worsening of narrow-angle glaucoma, acute eye pain, blurred vision, paradoxical bronchospasm, wheezing, exacerbation of chronic obstructive pulmonary disease symptoms, drowsiness, aching, flushing, upper respiratory tract infection, palpitations, taste perversion, elevated heart rate, sinusitis, back pain and sore throat may occur after administrating the inhalation solution in the one or more containers; and (h) the adverse reaction data includes a list of one or more adverse events that may occur after administration of the inhalation solution in each of the one or more containers; the adverse events including chest pain, diarrhea, dyspepsia, nausea, leg cramps, bronchitis, lung disease, pharyngitis, pneumonia, and urinary tract infection.

Figure 5:
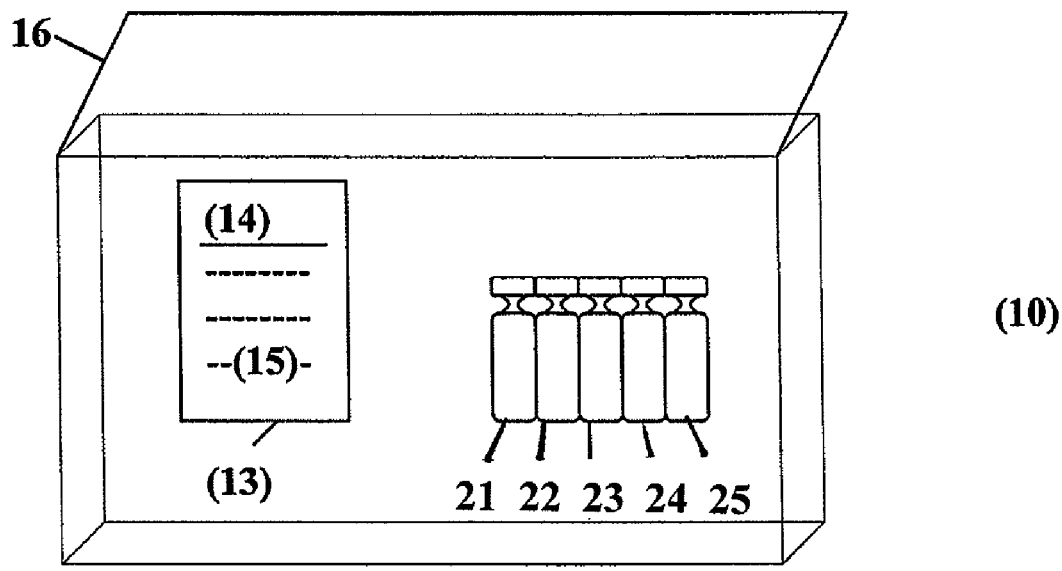
FIG. 5 depicts a non-limiting example of a unified prepackaged kit or system of the present invention.

The prepackaged inhalation system and/or kit may be provided in one of any number of forms, including, but not limited to, a box containing one or more prepackaged, unit dose vials or a box containing individual packages or pouches comprising one or more unit dose vials. For example, an embodiment of a unified prepackaged system and/or kit for treating COPD in patients is depicted in FIG. 5. Specifically, FIG. 5 depicts support package (10). Support package (10) may include, but is not limited to, a box, carton or any other enclosed container. The support package comprising one or more prepackaged, pre-filled dispensing containers (21-25). Each container comprising a premixed, premeasured inhalation solution. The inhalation solution comprising a unit dose of a therapeutically effective amount of albuterol and ipratropium for treating COPD. The inhalation solution may be provided in sterile and/or BAC-free form.

Support package (10) may also incorporate one or more labels (13) therein. One or more labels (13) may comprise indicia (14) indicating that the inhalation solution can be used to relieve symptoms associated with COPD, such as bronchospasm. The label may also comprise indicia (15) which provides instructions for using the inhalation solution to relieve such symptoms. As used herein "indicia" includes, but is not limited to, wording, pictures, drawings, symbols and/or shapes. A non-limiting example of the indicia that may appear on the one or more labels (13) is shown in FIG. 7. The one or more labels may be positioned on one or more surfaces of support package (10) or a separate sheet, or any combination thereof. Support package (10) may also incorporate lid (16) to enclose the packaging material therein.

The system and/or kit of the present invention may also include a label and/or instructions designed to facilitate user compliance. For example, in an embodiment, a system and/or kit of the present invention comprises packaging material containing one or more prepackaged vials comprising a sterile, premixed, premeasured unit dose of an inhalation solution comprising a therapeutic effective amount of albuterol and ipratropium. The packaging material may further comprise a label indicating that each vial can be used with a nebulizer for the relief of symptoms associated with COPD, such as bronchospasm. Such instructions may also include instructions on dosage for each nebulizer treatment, as well as instructions for administration, such as by nebulizer. The instructions may be positioned on one or more surfaces of the packaging material therein, or the instructions may be provided on a separate sheet, or any combination thereof.

The present invention is also directed to a method of treating symptoms associated with COPD, including bronchospasm, wherein a therapeutically effective amount of albuterol and ipratropium may be administered as a unit dose. Such unit dose may be in the form of a nebulizer solution.

In another embodiment, the present invention is directed to a method for inducing bronchodilation or providing relief of bronchospasm in a patient suffering from chronic obstructive pulmonary disease, said method comprising the step of:

(a) providing the patient a prepackaged therapeutic system comprising:
one or more dispensing containers; the one or more containers each prefilled with about 3 ml of a sterile, benzalkonium chloride-free, premixed, premeasured aqueous inhalation solution comprising a unit dose of a therapeutically effective amount of albuterol and ipratropium bromide; wherein the amount of albuterol is about 2.5 mg and the amount of ipratropium bromide is about 0.5 mg; the inhalation solution in each of the one or more containers is suitable for nebulization in a nebulizer; the inhalation solution in each of the one or more containers has a long shelf life;

(b) providing the patient or prescriber of the prepackaged therapeutic system dosage, administration, contraindication and adverse reaction data pertaining to the inhalation solution in each of the one or more containers;

(c) wherein the contraindication data comprises data indicating that the inhalation solution in each of the one or more containers is contraindicated for humans with hypersensitivity to atropine and derivatives thereof; and (d) wherein the adverse reaction data comprises data indicating that precipitation or worsening of narrow-angle glaucoma, acute eye pain, blurred vision, paradoxical bronchospasm, wheezing, exacerbation of chronic obstructive pulmonary disease symptoms, drowsiness, aching, flushing, upper respiratory tract infection, palpitations, taste perversion, elevated heart rate, sinusitis, back pain and sore throat may occur after administrating the inhalation solution in the one or more containers.

In the present method, the dosage and administration data may inform the patient or prescriber the recommended dose of the inhalation solution in each of the one or more containers is about 2.5 mg of albuterol and 0.5 mg impratropium bromide in 3 ml of an aqueous solution administered 4 times per day by nebulization with up to 2 additional recommended doses allowed per day, if needed. The adverse reaction may also inform the patient or prescriber that immediate hypersensitivity reactions to the inhalation solution in each of the one or more containers may occur after administration of the inhalation solution, said hypersensitivity reactions including urticaris, angioedema, rash, pruritis, oropharyngeal, edema, bronchospasm, and anaphylaxis. The adverse reaction data may further inform the patient or prescriber that allergic-type reactions may occur after administrating the inhalation solution in the one or more containers, including skin rash, prurities, and urticaria. Also, the adverse reaction data may include a preprinted list of one or more adverse events that may occur after administrating the inhalation solution, said adverse events comprising chest pain, diarrhea, dyspepsia, nausea, leg cramps, bronchitis, lung disease, pharyngitis, pneumonia, and urinary tract infection.

In another alternative embodiment, the present invention is directed to a method for inducing bronchodilation or providing relief of bronchospasm in a patient suffering from chronic obstructive pulmonary disease, said method comprising the step of:

(a) providing a patient the prepackaged therapeutic system comprising:
one or more dispensing containers; the one more containers each prefilled with about 3 ml of a sterile, stable, premixed, premeasured aqueous inhalation solution free of benzalkonium chloride; the inhalation solution consisting of water, edetate disodium, sodium chloride, and an acid to adjust the pH of the inhalation solution to about 4, and a unit dose of a therapeutically effective amount of albuterol and ipratropium bromide, wherein the amount of albuterol is about 2.50 mg/3 ml and the amount of ipratropium bromide is about 0.5 mg/3 ml; the inhalation solution in each of the one or more containers is suitable for nebulization in a nebulizer;

(b) providing the patient or prescriber the prepackaged therapeutic system efficacy, dosage, administration, contraindication and adverse reaction data pertaining to the inhalation solution in each of the one or more containers;

(c) wherein the dosage and administration data informs the patient or prescriber that the recommended dose of the inhalation solution in each of the one or more containers is about 2.5 mg of albuterol and 0.5 mg impratropium bromide in 3 ml of an aqueous solution administered 4 times per day by nebulization with up to 2 additional recommended doses allowed per day, if needed;

(d) wherein the contraindication data comprises information indicating that the inhalation solution in each of the one or more containers is contraindicated for humans with hypersensitivity to atropine and derivatives thereof;

(e) wherein the adverse reaction data informs the patient or prescriber that immediate hypersensitivity reactions to the inhalation solution in each of the one or more containers may occur after administrating the inhalation solution in the one or more containers, said hypersensitivity reaction including urticaris, angioedema, rash, pruritis, oropharyngeal, edema, bronchospasm, and anaphylaxis;

(f) wherein the adverse reaction data informs the patient or prescriber that possible allergic-type reactions may occur after administering the inhalation solution in the one or more containers, including skin rash, prurities, and urticaria;

(g) wherein the adverse reaction data informs the patient or prescriber that precipitation or worsening of narrow-angle glaucoma, acute eye pain, blurred vision, paradoxical bronchospasm, wheezing, exacerbation of chronic obstructive pulmonary disease symptoms, drowsiness, aching, flushing, upper respiratory tract infection, palpitations, taste perversion, elevated heart rate, sinusitis, back pain and sore throat may occur after administrating the inhalation solution in the one or more containers; and (h) the adverse reaction data includes a preprinted list of one or more adverse events that may occur after administration of the inhalation solution in each of the one or more containers; the adverse events comprising chest pain, diarrhea, dyspepsia, nausea, leg cramps, bronchitis, lung disease, pharyngitis, pneumonia, and urinary tract infection.

In an alternative embodiment, the method of the present invention comprises the step of administering to a patient a therapeutically effective amount of albuterol and ipratropium. Such solution may also be prepackaged, premixed, premeasured, BAC-free and/or sterile. Such solution may also be in a single unit dose vial.

In another alternative embodiment, the method of the present invention comprises the step of administering to a patient in need an inhalation solution comprising a therapeutically effective amount of albuterol and ipratropium. The inhalation solution being administered by nebulizer, more preferably a jet nebulizer connected to an air compressor with adequate air flow.

In yet another alternative embodiment, in reference to FIGS. 1-4, the method of the present invention comprises the steps: (i) placing an inhalation solution comprising a therapeutically effective amount of albuterol and ipratropium (1) into a nebulizer cup (2). The nebulizer may be powered by attachment to compressed gas cylinders or an electrically driven compressor; (ii) using a "T" adapter (3) to fit the nebulizer cup lid (4) to a mouthpiece (5) or facemask (6); (iii) drawing the inhalation solution (1) up by the velocity of a gas jet and fragmenting it into an aerosol; (iv) passing the aerosol through the mouthpiece (5) or facemask (6) to the patient (7) afflicted with bronchospasm; and (v) the patient continues breathing until no more mist is formed in the nebulizer chamber (8). This may occur in about 5-15 minutes.

In one alternative embodiment, the usual starting dosage for patients may be about 2.50 mg albuterol and 0.5 mg ipratropium administered 3 or 4 times daily, as needed by nebulization. To administer these amounts of albuterol and ipratropium, the entire contents of one unit dose vial (e.g., about 3.0 mg/3 ml albuterol sulfate and 0.5 mg/3 ml ipratropium bromide) may be used. Preferably, the nebulizer flow rate is adjusted to deliver the albuterol and ipratropium over 5 to 15 minutes.

Further, in an alternative embodiment, the method of the present invention comprises the steps: (i) preparing an inhalation solution comprising a therapeutically effective amount of albuterol and ipratropium by diluting one or more solutions comprising the ipratropium or albuterol; and (ii) administering the inhalation solution to a patient in need thereof.

The present invention also provides a process for making a prepackaged, sterile, premixed, premeasured, and/or BAC-free inhalation solution comprising a single unit dose of a therapeutically effective amount of albuterol and ipratropium. In such an embodiment, the method of the present invention comprises one or more of the following steps: (i) adding at least a therapeutically effective amount of albuterol and ipratropium in a carrier, such as water; (ii) sterilizing the solution and sealing the container. An osmotic adjusting agent may be added to adjust the isotonicity of the solution. Preferably, the solution of the present invention is isotonic, and an osmotic adjusting agent may be added to adjust the isotonicity of the solution to about 280 to about 320 mOsm/kg. Additionally, an acid (e.g., hydrochloride) may be added to adjust the pH of the solution to a level of about 3.0 to about 5.0, preferably about 4.0.

In another embodiment, a process for making an inhalation solution of the present invention comprises one or more of the following steps: (i) adding at least a therapeutically effective amount of albuterol and ipratropium in a carrier such as water; (ii) placing the mixture in a container, and sterilizing the mixture by steam sterilization, or any other sterilizing means known in the art. Each albuterol and ipratropium mixture being filled into a vial, and then packaged, stored and/or used directly. Here, the resulting mixture is stable, and after sterilization, it can be dispersed, if necessary, into multiple mixtures each containing a unit dose of a therapeutically effective amount of albuterol and ipratropium.

Osmotic adjusting agents that may be used include, but are not limited to, sodium chloride, potassium chloride, zinc chloride, calcium chloride and mixtures thereof. Other osmotic adjusting agents may also include, but are not limited to, mannitol, glycerol, and dextrose and mixtures thereof. In an alternative embodiment, the present invention may comprise about 0.4 to about 1.0 weight percent ionic salt. Preferably, the present invention comprises 0.9 wt % of an osmotic adjusting agent.

In an alternative embodiment, the inhalation solution of the present invention may be prepared as follows: (i) fitting a stainless steel formulation tank with a bottom drain and a tri-blender for mixing; (ii) filling the tank with approximately 95% of the required amount of Purified Water USP at a temperature of between 18° C. to 25° C.; while mixing, (iii) adding EDTA USP, hydrochloric acid, and at least a therapeutically effective amount of Albuterol Sulfate USP and Ipratropium Bromide to the tank; (iv) continue mixing until all chemical components are dissolved; (v) adding Purified Water USP to adjust the final volume, if necessary, thus producing an albuterol and ipratropium bromide mixture.

Figure 6:
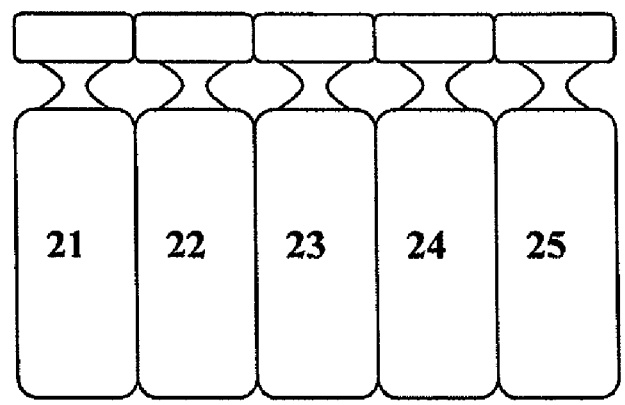
FIG. 6 depicts a non-limiting example of one or more pre-filled containers comprising the inhalation system of the present invention.
Figure 8:
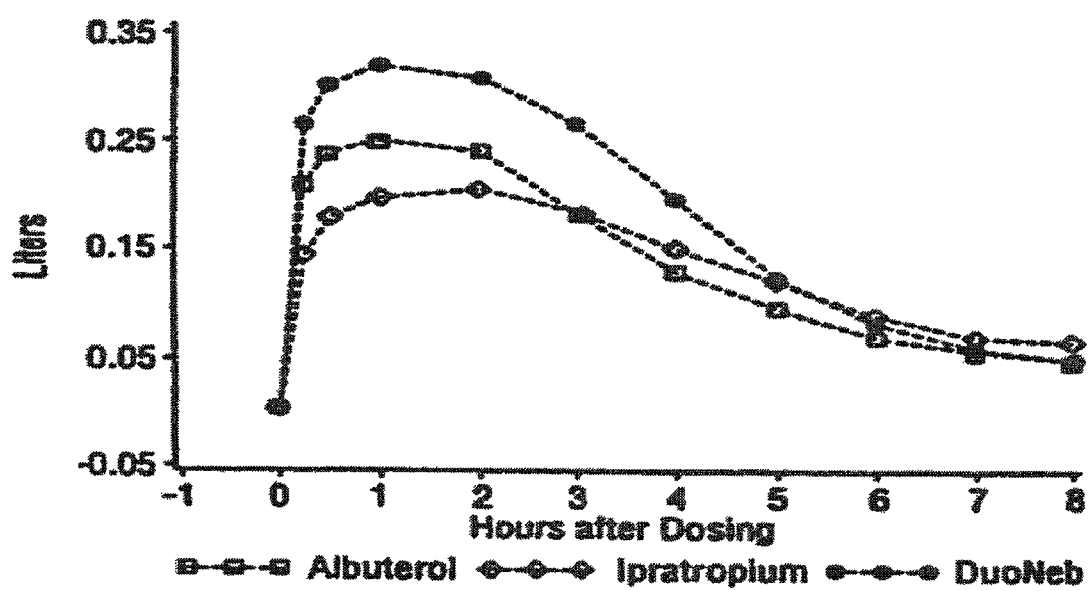
FIG. 8 is a graph illustrating the time course of $FEV_1$ response after dosing with albuterol alone, ipratropium alone, and the combination of albuterol and ipratropium according to the invention.
Figure 5:
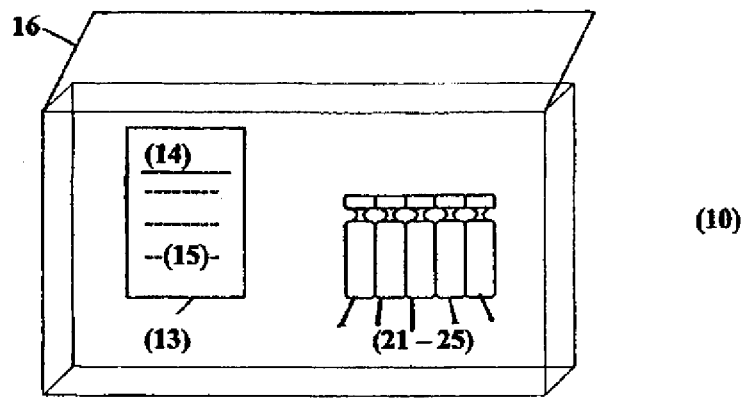
Figure 6:
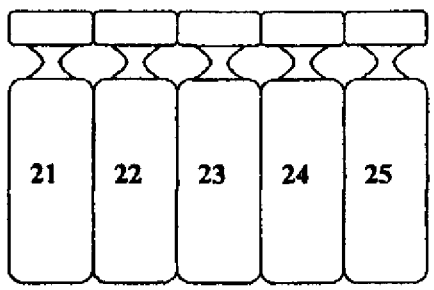

From the formulation tank, the albuterol and ipratropium mixture may be pumped through sanitary delivery lines directly into a form-fill-seal (FFS) machine. The albuterol and ipratropium mixture may pass through a 0.2 micron sterilizing cartridge filter, then into a reservoir tank, through a second 0.2 micron sterilizing cartridge filter to the filling nozzles within the sterile air shower compartment, and subsequently into formed vials of low density polyethylene (LDPE). The albuterol and ipratropium mixture may be sterile filled into the vials such that each vial contains a single unit dose of a therapeutically effective amount of albuterol. The filled vials may then be sealed. The FFS machine may form, fill and seal the vials in a continuous operation under aseptic conditions, thus producing a sterile product. For example, cards of five filled vials (FIG. 6) may be overwrapped into a protective laminated foil pouch using an autowrapper machine. Six to twelve such pouches may then be packaged in a shelf carton, thus forming a prepackaged therapeutic system for treating COPD in patients. An appropriate label and instructions may be added in the shelf carton.

The present invention is also directed to a method of forming a unit-dose nebulizer solution comprising the step of: (i) preparing a mixture containing a therapeutically effective amount of albuterol and ipratropium bromide in a pharmaceutically acceptable carrier. Said mixture being suitable for nebulization in a nebulizer.

Additionally, the present invention is directed to a method of making a prepackaged, stable, premeasured, and/or premixed aqueous nebulizer solution for reducing medication error and enhancing therapeutic compliance of an individual suffering from chronic obstructive pulmonary disease. In one embodiment, the method may comprise the steps of adding water, albuterol sulfate and ipratropium bromide into a container at a temperature between about 2° C. and about 70° C., or about 2° C. and about 50° C., or about 2° C. and about 30° C., or about 2° C. and about 25° C., or about 5° C. and about 25° C., preferably about 18° C. and about 25° C. to form a solution, wherein the final concentration of the albuterol and ipratropium bromide in the solution ranges from about 0.06 wt. % to about 0.1 wt. % albuterol and about 0.03 wt. % to about 0.1 wt. % ipratropium. The present method may also comprise the step of adjusting the pH of said solution to about 3.0 to about 4.0, preferably 3.5. The method of the present invention may further comprise the step of adding hydrochloric acid to adjust the pH of the inhalation solution. The method of the present invention may further comprise adding sufficient osmotic adjusting agent to the solution so that the isotonicity of the solution is from about 280 mOsm/kg to about 320 mOsm/kg. The present method may further require filling the solution into one or more dispensing vials, each vial being filled with about 0.1 ml to about 5 ml, or about 0.1 ml to about 2.25 ml, or about 0.1 ml to about 3.0 ml, about 0.5 ml to about 3.0 ml, or about 0.5 ml to about 2.0 ml, or about 0.1 ml to about 2 ml, preferably about 0.5 ml to about 1 ml, about 2 ml, or about 3 ml of the solution such that the solution in the each vial comprises a unit dose of a therapeutically effective amount of albuterol and ipratropium bromide. Also, in another alternative embodiment, the stability of the solution in the one or more dispensing containers is such that the solution is therapeutically effective following storage for 12 months at 25° C. The solution may be suitable for nebulization in a nebulizer.

The method may further comprise the step of sterile sealing the one or more vials after the solution is filled in the one or more vials. The method may further comprise the step of filing the nebulizer solution into the one or more low density polyethylene dispensing vials, wherein the solution filled in the one or more dispensing vials comprises about 0.4 wt. % to about 1.0 wt. % ionic salt, and the solution filled in the one or more dispensing vials comprises about 0.9% of an osmotic adjusting agent. The method further comprising the step of adding albuterol and ipratropium comprises adding sufficient albuterol and ipratropium so that the concentration of albuterol is about 0.083 wt. % and the concentration of ipratropium bromide is about 0.017 wt. % in the solution.

Drugs administered by nebulization play a major role in the treatment of COPD. It has been shown that some patients have difficulty inhaling sufficient amounts of the prescribed medication from a nebulizer and this may be a reason for treatment failure. However, one of the drawbacks of nebulization therapy is the number of times it must be performed each day, and the amount of time each treatment takes. For example, an individual may be required to receive 4 doses of inhalation solution per day by nebulization. In some instances, each nebulizer treatment takes about 15 minutes, or more to deliver a 2.5 ml fill volume of a bronchodilator, though the amount of time may vary depending on the model of the nebulizer used. Thus, in one day, an individual may be required to spend an hour or more to receive the necessary dosage of albuterol and ipratropium to induce bronchodilation or obtain relief of bronchospasm associated with COPD, for example. The time requirements for nebulization therapy can be burdensome, and cause individuals to skip required dosages during the day. The impact of not following the prescribed dosage regimen could compromise the individual's condition.

In one alternative embodiment, the volume of the albuterol/ipratropium inhalation solutions of the present invention is about 0.1 ml to about 2.25 ml, or about 0.1 ml to about 2 ml, or about 1 ml to about 2 ml, or about 1.5 ml to about 2 ml, preferably about 1 ml, about 1.5 ml, about 2.0 ml, or about 2.25 ml. In another alternative embodiment, the volume of the albuterol/ipratropium inhalation solution of the present invention is about 0.05 ml to about 1.0 ml; 0.1 ml to about 0.9 ml; 0.1 ml to about 0.8 ml; 0.1 ml to about 0.7 ml; 0.1 ml to about 0.6 ml; 0.1 ml to about 0.5 ml; 0.1 ml to about 0.4 ml; 0.1 ml to about 0.3 ml; 0.1 ml to about 2.0 ml. In one preferred embodiment the fill volume of the albuterol/ipratropium inhalation solution of the present invention is from about 0.05 ml to about 0.4 ml, preferably from about 0.1 ml to about 3.0 ml, more preferably about 0.25 ml. While no clinical trials or other experiments were carried out on these volumes, it is believed that such volumes would be more beneficial over conventional nebulizer solutions (e.g. 2.5 ml or 3.0 ml fill volume) because they will enable the individual to receive more medication (e.g., albuterol and ipratropium) in less time during each nebulization treatment. Also, it is believed that the fill volumes of the present invention will minimize common handling complications with nebulizer therapy, and it may extend the life of the nebulizer.

In one alternative embodiment, the fill volumes of the present invention may reduce the time of each nebulization treatment by at least 20%, 30%, 40%, 50%, 60%, 70% or 80% or more over conventional nebulizer treatments (e.g. 2.5 ml or 3 ml fill volume). In another alternative embodiment, the fill volumes of the present invention may reduce each nebulization treatment to about or less than about 12, 11, 10, 9, 8, 7, 6, 5, 4, 3, 2, 1 minutes, or any range therebetween less over conventional nebulizer treatments (e.g. 2.5 ml or 3.0 ml fill volume). Reducing the amount of time to complete the treatment means individuals will be more likely to comply with the prescribed dosing regimen and achieve optimal benefit from the medication prescribed.

Another drawback of conventional nebulizer treatments is the loss of medication during administration. Conventional nebulizer solutions comprise about 2.5 ml fill volume of inhalation solution, or more. For example, when nebulizing an inhalation solution comprising 2.5 ml or more, about 0.7 ml of the solution remains in the nebulizer system after treatment, though the amount may vary depending on the model of the nebulizer used. In these instances, the individual is not receiving the prescribed dosage or optimum dosage of inhalation medication. For example, in one day, due to the residual medication remaining in the nebulizer system after each treatment, an individual fails to receive approximately 2.1 ml, or more of the prescribed daily amount of medication.

It is believed that the fill volumes of the albuterol/ipratropium inhalation solutions of the present invention will result in lesser amounts of solution remaining in the nebulizer system after treatment, when compared to conventional inhalation solutions (e.g. 2.5 ml or 3 ml fill volume). Less solution remaining in the nebulizer system means more medication (e.g., albuterol and ipratropium) administered to the individual during each treatment. In one alternative embodiment, the amount of solution remaining in the nebulizer system after each treatment may be less than 0.50 ml, or less than 0.30 ml, or less than 0.20 ml or less than 0.10 ml or less than 0.05 ml of the albuterol/ipratropium inhalation solutions of the present invention, e.g. an inhalation solution comprising 2.5 mg albuterol and 0.5 mg ipratropium bromide.

Important factors to effective nebulizer treatment is deep inspiration to ensure deep penetration of the medication into the lungs, and steady breath-holding to ensure good retention of the medication in the lungs. It is believed that administering a fill volume less than 2.0 ml, preferably from about 0.1 ml to about 0.3 ml, more preferably about 0.25 ml of an inhalation solution into a nebulizer, for example, will optimize the therapeutic effect of the individual's deep inspiration efforts during treatment, and will optimize the therapeutic effect of the individual's breath-holding efforts as well. This is due to the shorter treatment time and increased concentration of the albuterol and ipratropium in the solution.

Accordingly, in one alternative embodiment, the present invention is a method of facilitating patient care, reducing medication error, reducing nebulizer treatment time, improving the efficiency and efficacy of nebulizing therapy or enhancing therapeutic compliance of an individual suffering from COPD. In one alternative embodiment, such method may comprise the step of placing about 0.1 ml to about 2.0 ml of the albuterol/ipratropium inhalation solutions of the present invention into a chamber of a nebulizer. The nebulizer having a mouthpiece or facemask associated with the chamber of the nebulizer. The mouthpiece or facemask is positioned in close proximity to the individual's mouth or face. The inhalation solution may be passed in a mist form from the nebulizer chamber through the mouthpiece or facemask to the individual while the individual breathes into the mouthpiece or facemask. The individual continues breathing into the mouthpiece or facemask until the nebulization treatment is finished. This may take about or less than about 12, 11, 10, 9, 8, 7, 6, 5, 4, 3, 2, 1 or 0.5 minutes, or any range therebetween. In another alternative embodiment, the treatment may be finished in about 60, 50, 40, 30, 20, 10, 5 or 1 second, or any range therebetween. In an alternative embodiment, the nebulization treatment is finished when at least substantially all the mist is removed from the nebulizer chamber. This may take about or less than about 12, 11, 10, 9, 8, 7, 6, 5, 4, 3, 2, 1 or 0.5 minutes, or any range therebetween. In an alternative embodiment, it may take about 60, 50, 40, 30, 20, 10, 5 or 1 second, or any range therebetween.

In another alternative embodiment, the system of the present invention comprises one or more dispensing containers prefilled with about 0.1 ml to about 2.0 ml, or about 0.1 ml to about 1.0 ml; 0.1 ml to about 0.9 ml; 0.1 ml to about 0.8 ml; 0.1 ml to about 0.7 ml; 0.1 ml to about 0.6 ml; 0.1 ml to about 0.5 ml; 0.1 ml to about 0.4 ml; 0.1 ml to about 0.3 ml; 0.1 ml to about 2.0 ml; about 0.5 ml to about 2.0 ml, or about 0.1 ml to about 2.25 ml, or about 1.0 ml to about 2.0 ml, or about 2.0 ml to about 2.4 ml of a premixed, premeasured, aqueous inhalation solution comprising a single unit dose of a therapeutically effective amount of albuterol and ipratropium bromide.

In one preferred embodiment, the present invention comprises 0.05 ml to about 0.4 ml, preferably from about 0.1 ml to about 0.3 ml, more preferably about 0.25 ml. The amount of albuterol may range from about 0.60 mg to about 5.0 mg, preferably about 2.5 mg. The amount of ipratropium bromide may range from about 0.01 mg to about 1.0 mg, preferably about 0.5 mg. In another alternative embodiment, the amount of albuterol may range from about 2.0 mg to about 3.0 mg, preferably about 2.5 mg. The solution may be suitable for nebulization in a nebulizer, and the solution may be stable, in that the inhalation solution is therapeutically effective following storage for 12 months at 25° C., for example. Also, in another embodiment, the inhalation solution in each of the one or more containers comprise a preservative or any other suitable anti-microbial agent, such as benzalkonium chloride, or may be preservative free. In one alternative embodiment, the inhalation solution may comprise 0.001% to about 2.0%, or 0.001% to about 0.5%, or about 0.01% to about 0.1% of a preservative, such as benzalkonium chloride, for example. The inhalation solution may further comprise sodium chloride, water, and an acid to adjust the pH of the inhalation solution to about 4, preferably about 3.5.

The system may further comprise a label that indicates that the inhalation solution can be used to relieve bronchospasm associated with chronic obstructive pulmonary disease. In one alternative embodiment, the label may comprise indicia comprising efficacy, dosage, administration, contraindication and adverse reaction data pertaining to the inhalation solution in each of the one or more containers. The contraindication data may comprise data indicating that the inhalation solution in each of the one or more containers is contraindicated for humans with hypersensitivity to any of the ingredients contained in the inhalation solution. Also, the adverse reaction data may comprise data indicating that lung disease, bronchitis, diarrhea or phargaryngitis may occur after administration of the inhalation solution. The dosage and administration data may also comprise data indicating that the recommended dose of the inhalation solution in each of the one or more containers may be administered 1, 2, 3, 4, 5, 6, 7 or 8 times per day by nebulization.

The present invention is also directed to a method of reducing medication error and enhancing therapeutic compliance of an individual suffering from chronic obstructive pulmonary disease. In one such embodiment, the method comprises the step of administrating to the individual at least one or more dispensing vials of the inhalation solution described herein, for example. Dispensing vials may include, but are not limited to, any container comprising glass, low density polyethylene, or any other material capable of preventing the solution from leaking out of the container. The vial may be enclosed by any conventional means, including but not limited to, screw cap, heat seal, snap-on top, flip-top, twist-off stopper, peel away top, and the like.

In accordance with the present invention, the albuterol/ipratropium inhalation solution may be stored in or dispensed from any dispensing vial made of suitable plastic material. For example, the dispensing vial may be constructed of any suitable elastomeric material, such as olefin-based materials, including but not limited to, polyethylene, ethylene-propylene copolymers, ethylene-vinyl acetate copolymers, ethylene-acrylic ester copolymers, iononomers, and combinations thereof. Furthermore, polymers having barrier properties, such as polyvinylidene chloride and ethylene-vinyl alcohol copolymers, as well as polymers such as polyvinyl chloride, polyester, polyamide and polyurethanes may also be used.

In an alternative embodiment, the present invention also comprises a device for use in the relief of symptoms associated with COPD, including bronchospasm. Such device may take the form of a label, written instructions or any other form incorporating indicia thereon. The device may comprise indicia that indicates that a patient suffering from symptoms associated with COPD can be treated with at least one prepackaged, sterile, premixed, premeasured and/or BAC-free inhalation solution comprising a unit dose of a therapeutically effective amount of albuterol and ipratropium in a single vial. The inhalation solution being suitable for nebulization in a nebulizer. The device may also comprise indicia that provides instructions for utilizing the inhalation solution to treat said symptoms in patients.

EXAMPLES

To evaluate the efficacy and safety of the inhalation solution of the present invention, a double-blind, randomized, positive control trial was performed. The design, results and conclusion of the study are described in detail below.

Patients

A total of 863 patients were initially randomized for enrollment in the trial. To be eligible for enrollment, patients had to meet the criteria described in Table 3.

TABLE 3

Inclusion/Exclusion Criteria

| Design Element | Description |
| --- | --- |
| Inclusion Criteria | Diagnosis with COPD with an $FEV_1$ between 25% and 65% of the normal predicted value.<br>Age > 40 years.<br>Regular use of one or more bronchodilators for a minimum of 3 months prior to enrollment.<br>History of at least 10 pack-years of smoking.<br>Ability to refrain from the use of theophylline, salmeterol and oral $\beta_2$ agonists for the duration of the trial (as judged by the investigator).<br>Ability to safely complete a 6-minute walk.<br>Willingness to provide informed consent. |

TABLE 3-continued

Inclusion/Exclusion Criteria

Design
Element  Description

Exclusion  Diagnosis of anthracosis, silicosis, any parenchymal
Criteria   disease not attributable to COPD, polycythemia, or
           pulmonale, hypoxia, or a primary diagnosis
           attributable to allergic rhinitis, atopy, or COPD.
           Clinically significant obstructive urinary disease,
           narrow-angle glaucoma, unstable angina pectoris or
           myocardial infarction in the past 6 months, known
           drug abuse within the last 12 months, or
           hospitalization for pulmonary exacerbation
           within the past 2 months.
           Known hypersensitivity to any component of the
           study medications.
           Investigational drug use within 30 days of first
           dose of study medication.
           Pregnancy or breastfeeding.

Interventions

The doses of each individual agent and the ipratropium and albuterol combination were as shown in Table 4 below. All study medications were administered 4 times per day (ideally every 6 hours) by inhalation using a PARI LC PLUS™ nebulizer and PARI PRONEB® compressor. Concomitant use of bronchodilators was restricted during the trial. Oral and inhaled steroic use was permitted throughout the trial, provided that dosing remained constant.

TABLE 4

| Study Medication | Albuterol (base) | Ipratropium bromide |
|---|---|---|
| Albuterol alone | 2.5 mg/3 ml | |
| Ipratropium alone | | 0.5 mg/3 ml |
| Albuterol and Ipratropium Combination | 2.5 mg/3 ml | 0.5 mg/3 ml |

Efficacy Results

Of the 863 patients who were randomized and began treatment, 289 withdrew prematurely from the trial, including 28 patients who did not meet the inclusion/exclusion criteria and were inappropriately enrolled. A total of 663 patients received both the inhalation solution of the present invention and at least one other study medication and completed at least one post-dose measurement of $FEV_1$. These subjects contributed to the 647 evaluable comparisons in each portion of the primary analysis, as the majority of patients completed treatment on all three study medications.

The primary efficacy variable was the change from pre-dose to peak $FEV_1$ measured within 3 hours after dosing during the crossover phase of the trial. As can be seen in Table 5, the mean increase in $FEV_1$ was significantly higher for the albuterol and ipratropium combination than for either agent used alone. The improvement for the combination over albuterol alone was 23.6% and over ipratropium alone was 37.2%. The time course of $FEV_1$ response is shown in Table 8.

During the parallel phase of the trial, separate groups of patients self-administered only one of the three study medications during the final 6 weeks of the trial. Results for the parallel phase yielded results essentially identical to the crossover phase. The albuterol and ipratropium combination maintained the same magnitude of superiority over each component medication alone that was observed during the crossover phase in peak $FEV_1$ response.

Safety/Tolerability

Adverse reactions concerning the albuterol and ipratropium combination were evaluated from the clinical trials described above. Treatment-emergent adverse events that were reported by 1% or greater of patients are summarized by medication in Table 6. As can be seen, there were no differences between the albuterol and ipratropium combination and the individual medication in incidence of patients with adverse events across body systems.

TABLE 6

Adverse Event Reports
(ADVERSE EVENTS OCCURRING IN ≧1% OF TREATMENT GROUP(S) AND WHERE THE COMBINATION TREATMENT SHOWED THE HIGHEST PERCENTAGE)

| Body System COSTART Term | Albuterol n (%) | Ipratropium n (%) | Albuterol and Ipratropium Combination n (%) |
|---|---|---|---|
| NUMBER OF PATIENTS | 761 | 754 | 765 |
| N (%) Patients with A | 327 (43.0) | 329 (43.6) | 367 (48.0) |
| BODY AS A WHOLE | | | |
| Pain | 8 (1.1) | 4 (0.5) | 10 (1.3) |
| Pain chest | 11 (1.4) | 14 (1.9) | 20 (2.6) |
| DIGESTIVE | | | |
| Diarrhea | 5 (0.7) | 9 (1.2) | 14 (1.8) |
| Dyspepsia | 7 (0.9) | 8 (1.1) | 10 (1.3) |
| Nausea | 7 (0.9) | 6 (0.8) | 11 (1.4) |
| MUSCULO-SKELETAL | | | |
| Cramps leg | 8 (1.1) | 6 (0.8) | 11 (1.4) |
| RESPIRATORY | | | |
| Bronchitis | 11 (1.4) | 13 (1.7) | 13 (1.7) |
| Lung Disease | 36 (4.7) | 34 (4.5) | 49 (6.4) |
| Pharyngitis | 27 (3.5) | 27 (3.6) | 34 (4.4) |
| Pneumonia | 7 (0.9) | 8 (1.1) | 10 (1.3) |
| UROGENITAL | | | |
| Infection urinary tract | 3 (0.4) | 9 (1.2) | 12 (1.6) |

Additional adverse reactions reported in more than 1% of patients treated with the albuterol and ipratropium combination included constipation and voice alterations.

TABLE 5

Efficacy Results in Crossover Phase

| | Combination vs. Albuterol | | | | Combination vs. Ipratropium | | | |
|---|---|---|---|---|---|---|---|---|
| Parameter | n | Combination mean | Albuterol mean | p value | n | Combination mean | Ipratropium mean | p value |
| Peak $FEV_1$ (liters) | 647 | 0.387 | 0.313 | <0.001 | 647 | 0.387 | 0.282 | <0.001 |

Example 2

Example 2 is a prophetic example of a nebulizable inhalation solution of the present invention having about 0.5 ml fill volume. It is provided to illustrate, but not limit, the present invention. It is believed that prophetic Example 2 would be suitable for inducing bronchodialation or providing relief of bronchospasm in an individual 2 to 12 years suffering from COPD. The inhalation solution may be a sterile, premixed, premeasured single unit dose. It may also comprise all other attributes, features and ingredients of the various embodiments of the present invention, as described herein. Prophetic Example 2 may be administered to an individual in accordance with one or more of the modes of administration described herein.

TABLE 9

| Ingredient | Composition (% w/w) | Range (% w/w) |
| --- | --- | --- |
| Albuterol sulfate (expressed as sulfate) | About 0.30 or about 0.15 (expressed as sulfate) | 0.1 to 2.5 |
| Ipratropium (anydrous) Bromide | 0.102 | 0.008 to 0.5 |
| EDTA | 0.01 | 0.001 to 0.2 |
| Sodium Chloride | 0.82 | 0 to 0.9 |
| 1N HCl | 0.046 | 0 to 1.4 |
| Purified water | q.s. | q.s. |

The figures and attachments herein are presented for illustrative proposes only. They are not intended to limit the scope of the invention. Further, it should be understood that various changes and modifications to the presently preferred embodiment described herein will be apparent to those skilled in the art. Such changes and modifications can be made without departing from the spirit and scope of the present invention and without diminishing its attendant advantages. It is therefore intended that such changes and modifications be covered by the appended claims.

Also, the invention may suitably comprise, consist of or consist essentially of the elements described herein, and the invention described herein suitably may be practiced in the absence of any element that is not specifically disclosed herein.

We claim:

1. A method of inducing bronchodilation or providing relief of bronchospasm in an individual suffering from chronic obstructive pulmonary disease, said method comprising the step of:
   (a) providing one or more single dispensing containers; the one or more containers each being prefilled with a content of about 0.1 ml to about 0.5 ml of a premixed, premeasured aqueous inhalation solution comprising a single unit dose of a therapeutically effective amount of albuterol and ipratropium bromide; wherein the amount of albuterol is about 0.6 mg to about 5.0 mg and the amount of ipratropium bromide is about 0.1 mg to about 1.0 mg; and
   (b) administering the inhalation solution in one of the containers from a nebulizer chamber such that the mist is removed from the nebulizer chamber in less than 12 minutes.

2. The method of claim 1, wherein each of the one or more containers is prefilled with about 0.5 ml of the inhalation solution.

3. The method of claim 1, further comprising the step of providing dosage, administration, contraindication and adverse reaction data pertaining to the inhalation solution in each of the one or more containers.

4. The method of claim 1, wherein the mist is removed from the nebulizer chamber in less than 10 minutes.

5. The method of claim 1, wherein the mist is removed from the nebulizer chamber in less than 8 minutes.

6. The method of claim 1, wherein the mist is removed from the nebulizer chamber in less than 6 minutes.

7. The method of claim 1, wherein the mist is removed from the nebulizer chamber in less than 4 minutes.

8. The method of claim 1, wherein said amount of albuterol ranges from about 2.0 mg to about 3.0 mg.

9. The method of claim 1, wherein the albuterol is albuterol base, and said amount of albuterol base is about 2.5 mg and the amount of ipratropium is about 0.5 mg.

10. The method of claim 1, wherein the inhalation solution in each of the one or more containers is sterile.

11. The method of claim 1, wherein the inhalation solution in each of the one or more containers is free of benzalkonium chloride.

12. The method of claim 1, wherein the system further comprises a label which indicates that the inhalation solution can be used to relieve bronchospasm associated with chronic obstructive pulmonary disease.

13. The method of claim 12, wherein said label comprises instructions for using the solution to relieve said bronchospasm.

14. The method of claim 1, wherein all of the mist is removed from the nebulizer chamber in less than 12 minutes.

* * * * *

UNITED STATES PATENT AND TRADEMARK OFFICE
CERTIFICATE OF CORRECTION

PATENT NO.        : 8,084,461 B2
APPLICATION NO.   : 11/037574
DATED             : December 27, 2011
INVENTOR(S)       : Chaudry et al.

It is certified that error appears in the above-identified patent and that said Letters Patent is hereby corrected as shown below:

In the Drawings

The drawing sheet(s) 3 of 5 consisting of Fig(s) 5 and 6 should be deleted and substitute therefore the attached drawing sheet(s) 3 of 5 consisting of Fig(s) 5 and 6.

Signed and Sealed this
Thirtieth Day of April, 2013

Teresa Stanek Rea
*Acting Director of the United States Patent and Trademark Office*